United States Patent [19]

Koenhen et al.

[11] Patent Number: 5,338,455

[45] Date of Patent: Aug. 16, 1994

[54] PROCESS FOR THE SEPARATION OF COMPONENTS IN AN ORGANIC LIQUID MEDIUM AND A SEMI-PERMEABLE COMPOSITE MEMBRANE THEREFOR

[75] Inventors: Dirk M. Koenhen, Dedemsvaart; Aloysius H. A. Tinnemans, Zeist, both of Netherlands

[73] Assignee: X-Flow B.V., Ah Almelo, Netherlands

[21] Appl. No.: 111,166

[22] Filed: Jun. 5, 1991

[30] Foreign Application Priority Data

Jun. 6, 1990 [NL] Netherlands ............... 9001275

[51] Int. Cl.$^5$ .............................. B01D 61/08
[52] U.S. Cl. .................... 210/654; 210/490; 210/500.36
[58] Field of Search .......... 210/651, 490, 500.35, 210/654, 500.36; 55/16, 158

[56] References Cited

U.S. PATENT DOCUMENTS

| 4,617,126 | 10/1986 | Funk et al. ............... 210/651 |
| 4,644,046 | 2/1987 | Yamada ................. 55/159 X |
| 4,802,984 | 2/1989 | Waite ............... 210/500.35 X |
| 4,865,745 | 9/1989 | Pasternak ............... 210/651 |
| 4,897,091 | 1/1990 | Pasternak et al. ........... 55/16 |
| 4,913,816 | 4/1990 | Waite ............... 210/500.34 X |
| 4,929,358 | 5/1990 | Koenitzer ............ 210/651 X |
| 4,982,051 | 1/1991 | Pasternak et al. ........ 210/651 X |

FOREIGN PATENT DOCUMENTS

| 0094050 | 11/1983 | European Pat. Off. . |
| 0174045 | 3/1986 | European Pat. Off. . |
| 0243876 | 4/1987 | European Pat. Off. . |
| 0312378 | 4/1989 | European Pat. Off. . |

OTHER PUBLICATIONS

Journal of Membrane Science, vol. 32, No. 2-3, Jul. 1987 (Amsterdam, NL), G. R. Bartels et al.: Structure-performance relationships of composite membranes: porous support densification.

Patent Abstracts of Japan, vol. 7, No. 191 (C-182) (1336), Aug. 20, 1983 & JP,A, 5892420 (Toyo Boseki K.K.), Jul. 1, 1983.

WPIL, Jun. 2, 1988, AN=88/193436, Derwent Publ. Ltd, (London, GB) & Patent Abstracts of Japan, vol. 12, No. 382 (C-535) (3229) Oct. 12, 1988 & JP,A, 63130105 (Mitsubishi Gas), & Chemical Abstracts, vol. 110, No. 6, Feb. 6, 1988.

Primary Examiner—Frank Spear
Attorney, Agent, or Firm—Brooks Haidt Haffner & Delahunty

[57] ABSTRACT

A semi-permeable composite with a porous substrate having a polymer network obtained by interfacial polymerization of a reactive polyfunctional monomer having reactive groups —NHR. ($R_1$ is H or a $C_1$-$C_{20}$ alkyl groups), —OH or —SH and a reactive polyfunctional material having —NCO reactive groups built from a polyalkylene oxide with terminal —OH groups and a polyisocyanate, and a process for separating components in an organic liquid medium by using said composite.

6 Claims, No Drawings

PROCESS FOR THE SEPARATION OF COMPONENTS IN AN ORGANIC LIQUID MEDIUM AND A SEMI-PERMEABLE COMPOSITE MEMBRANE THEREFOR

The present invention relates to a process for the separation of components in an organic liquid medium by means of a semi-permeable composite membrane with a porous carrier substrate on which a polymer network obtained by interfacial polymerisation is applied and to a semi-permeable composite membrane therefor.

Semi-permeable composite membranes are known from European patent application 0.311.912. As porous carrier one uses herewith preferably a polysulphone. On the porous carrier is applied by interfacial polymerisation poly-meta-phenylene tetrahydrofuran 2,3,4,5-tetracarboxamide. It is noted that such membranes are suitable for use in aqueous systems, in particular for removing salts from aqueous solutions.

Furthermore it is known from the European patent application 0.275.027 that one may remove by reverse osmosis materials which are dissolved or dispersed in an aqueous solution or dispersing medium wherein the said materials are separated from the solvent respectively dispersing medium. The membranes used herewith are selective permeable for certain components of the mixture to be separated. The here described known processes and membranes are developed for separation processes in water. Herein an aqueous feed solution is brought in contact with a surface of the reversd osmosis membrane under pressure. The water permeability of the membrane is promoted by the applied pressure.

Membranes for reverse osmosis in general may be prepared from a polymer, for example polyamide, as described in the U.S. Pat. No. 4,277,344. From more recent developments appears that thin film composite membranes in particular are suitable for reverse osmosis. Such membranes which have a good salt retention are described in the U.S. Pat. Nos. 4,520,044 and 4,606,943.

The U.S. Pat. No. 4,767,148 describes thin film composite membranes for reverse osmosis, which are manufactured by interfacial polymerisation of a polyfunctional primarily water soluble primary or secondary amine in an aqueous solution with a relatively water insoluble polyfunctional acyl halide in an organic solvent.

Thin film composite membranes in general are prepared by interfacial polymerisation. Mostly one uses reactions of polyfunctional amines with polyfunctional acid halides or polyfunctional isocyanates.

According to a known process a porous carrier substrate, in general a polysulphone ultra-filtration membrane is coated with a solution of one of the components whereafter the so coated membrane is brought into contact with a solution of the other reactive component wherein the respective solvents are inmiscible.

The reaction proceeds at the interface wherein a thin polymer film with separation properties is obtained.

For ultra-filtration membranes in general the membranes are manufactured by the phase inversion technique. Such membranes also may be used as carrier substrates for the manufacture of thin film composite membranes.

Examples of such membranes are described in the U.S. Pat. Nos. 3,926,748 and 4,039,440.

Sometimes one uses carrier substrates with big pores like microporous polypropylene (Celgard) and membranes prepared by the process of the U.S. Pat. No. 4,798,847.

These composite membranes in general have the same properties as silicone membranes manufactured by solution deposit as described in the U.S. Pat. No. 4,581,043, with this difference that possibly the thickness of the composite layer is thinner whereby productivity may be higher.

Composite membranes with a homogeneous coating are also used for reverse osmosis or ultra-filtration processes for the separation of solvents from hydrocarbons. A fluorine containing silicone coating is described in the U.S. Pat. No. 4,748,288.

An example of such processes for the preparation of membranes for use for the separation of aromates from saturates in amongst others pervaporation can be found in the European patent application 0 312 378.

The use of homopolymers for membrane applications has various disadvantages.

In the first place the choice of polymers is restricted, in particular in the cases where the membrane is in contact with liquids like in reverse osmosis, ultra-filtration and pervaporation. The choice herein is restricted to polymers which do not dissolve or do not excessively swell in the disperging medium or which have functional groups which are capable of causing cross-links.

So, for example, polyvinylalcohol is only suitable as a pervaporation or reverse osmosis membrane for aqueous applications after cross-links since otherwise the polymer would dissolve.

An other example is the use of polydimethyl siloxane as a membrane for removing lubricating oil (dewaxing) from a mixture of methyl ethyl ketone and toluene. Composite membranes with a polydimethyl siloxane coating show in such medium a too excessive swelling reason they cannot be used. To solve this problem one has to use a fluorized siloxane polymer, for example.

The Japanese patent 6 0032-897 describes a process for dewaxing sunflower oil, rape seed oil, cotton seed oil, maize oil, palm oil, coconut oil using a porous hollow fibre membrane which preferably is a microfilter. This membrane is no composite membrane as meant in the sense of the present invention.

Furthermore U.S. Pat. No. 4,595,507 describes a process for the separation of a solvent from deasphalted crude oil using a polysulphone membrane sulphonated in solution.

Usually a mixture of crude oil and hexane is led through the membrane having a pore size of 10-500 Å.

The U.S. Pat. No. 4,541,972 describes a cellulose-1,7-1,8-acetate membrane for the separation of polar solvents from oils. Herein are considered as solvents (m) ethanol or (iso)propanol and cyclohexanone, propylene carbonate, methylisobutyl ketone, tetrakis, chloro benzene or toluene.

The present invention aims a process for the separation of components in an organic liquid medium, for example toluene dissolved n-docosane using a semi-permeable composite membrane which is applied to a porous carrier substrate.

Herefor the present invention provides a process for the separation of components in an organic liquid medium with a semi-permeable composite membrane with a porous carrier substrate on which a polymer network obtained by interfacial polymerisation is applied characterized in that the organic liquid medium is brought in contact contact with such semi-permeable composite membrane of which the polymer network is built from a reactive polyfunctional monomer or oligomer or a prepolymer with as reactive groups —$NHR_1$ ($R_1$=H or alkyl with $C_1$-$C_{20}$), —OH or —SH and one reactive polyfunctional monomer or oligomer or prepolymer with as reactive groups —NCO.

By the present process based on reverse osmosis one may in an efficient manner separate a substance dissolved in an organic solvent, for example, n-docosane in toluene with a good flux and high retention.

Good results are obtained when the reactive polyfunctional monomer or oligomer or prepolymer or polymer with as reactive groups —NCO is built from a polyalkylene oxide with final —OH groups and an aromatic or aliphatic isocyanate either branched or not and either substituted or not with at least two —NCO groups.

As polyalkylene oxide one uses preferably poly(tetramethylene ether glycol) with the formula HO—($CH_2CH_2CH_2CH_2$—O)$_n$—H wherein n is an integer of $\geq 3$, preferably $\geq 6$.

A suitable polyalkylene oxide of the present invention is polypropylene glycol with the formula

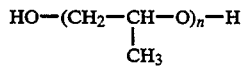

wherein n is an integer of $\geq 3$, preferably $\geq 15$.

According to the invention good results are obtained when use is made of a semi-permeable composite membrane built from a reactive polyfunctional monomer or oligomer or prepolymer or polymer with as reactive groups —NCO from a poly(butadiene) with terminal —OH groups and an aromatic or aliphatic isocyanate with at least two —NCO groups.

The process of the invention proceeds particularly favourable when use is made of a composite membrane of which on the carrier substrate a polymer network obtained by interfacial polymerisation is applied, which polymer network is built from a polyalkyl siloxane either branched or not with final —OH groups with the formula

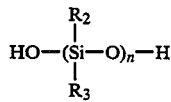

wherein $R_2$ and $R_3$ independently from each other represent a $C_1$-$C_{20}$ alkyl or aryl group either substituted or not and n is an integer of 2-100 or a copolymer thereof.

Good results are obtained by using a composite membrane of which the polymer network is built from a polyethylene imine and toluene diisocyanate.

Also one obtains good results by using a composite membrane of which the polymer network is built from N,N'-bis(3-aminopropylethylene diamine) and toluene diisocyanate.

Furthermore the invention relates to semi-permeable composite membranes with a porous carrier substrate for use in the process of the invention.

A suitable composite membrane of the invention is one wherein on the carrier substrate a polymer network obtained by interfacial polymerisation is applied which polymer network is built from a reactive polyfunctional monomer or oligomer or prepolymer with as reactive groups —$NHR_1$ ($R_1$=H or alkyl with $C_1$-$C_{20}$), —OH or —SH and one reactive polyfunctional monomer or oligomer or prepolymer with as reactive groups —NCO.

A suitable semi-permeable composite membrane of the invention is one of which the polymer network is built from a reactive polyfunctional monomer or oligomer or prepolymer or polymer with as reactive groups —NCO from a polyalkylene oxide with final —OH groups either branched or not and either substituted or not and an aromatic or aliphatic isocyanate with at least two —NCO groups wherein the polyalkylene oxide preferably is poly(tetramethylene ether glycol) with the formula HO—($CH_2CH_2CH_2CH_2$—O)$_n$—H wherein n is an integer of $\geq 3$, preferably $\geq 6$.

It is particularly favourable when the polyalkylene oxide is polypropylene glycol with the formula

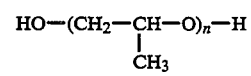

wherein n is an integer of $\geq 3$, preferably $\geq 15$.

Further a semi-permeable composite membrane is suitable when the reactive polyfunctional monomer or oligomer or prepolymer or polymer with as reactive groups —NCO is built from a poly(butadiene) with terminal —OH groups and an aromatic or aliphatic isocyanate with at least two —NCO groups.

Finally, for the separation of components in an organic liquid medium a semi-permeable composite membrane is effective when on the carrier substrate a polymer network obtained by interfacial polymerisation is applied which polymer network is built from a polyalkyl siloxane with terminal —OH groups either branched or not with the formula

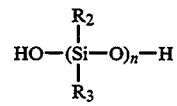

wherein $R_2$ and $R_3$ independently from each other represent a $C_1$-$C_{20}$ alkyl or aryl group either substituted or not and n is an integer of 2-100 or a copolymer thereof.

The invention will be explained by the following non-limiting examples.

EXAMPLE I

In a 1 liter round bottom flask provided with a distillation mount and an injection port with a rubber septum were introduced 9.1 g (7.8 Moles) poly(tetramethylene etherglycol) (Polymeg 1000$^R$, Quaker Oats Co.; OH contents 1.73 mmoles/g) and 915 ml toluene (pro analyse, Merck). From this solution under nitrogen atmosphere about 240 ml of a mixture of toluene and water was removed by azeotropic distillation. Subsequently the distillation mount was replaced by a reflux condenser while the solution remained under nitrogen atmosphere. To this solution were successively added by a syringe 2.75 g (15.8 mmoles) toluene diisocyanate (T-80$^R$, Bayer), i.e. molar ratio Polymeg 1000 / T-80=½, and 0.09 g [$CH_3(CH_2)_{10}CO_2$]$_2$ Sn[($CH_2$)$_3CH_3$]$_2$ as catalyst. Subsequently the reaction mixture was stirred during 3,5 hours at 65°-70° C. The resulting yellow brown solution contained 2.0%, by weight, prepolymer and a free toluene diisocyanate contents of about 15% (on basis of GPC analysis after modification with di-n-butylamine).

A wet flat support membrane of polyimide (0.35×0.12 m) prepared from a 16%, by weight, solution of a polyimide type (Lenzing P84) in DMF was applied to a cylindrical immersion body made from teflon. This support membrane was immersed during 15 minutes in a water phase with 0.5%, by weight, $NH_2$—$CH_2CH_2CH_2$—NH—$CH_2$—$CH_2$—NH—$CH_2CH_2CH_2$—$NH_2$, 0.05%, by weight, poly(vinyl alcohol) (Mowiol 4-88$^R$ Hoechst) and 0.04% by weight, sodium dodecyl sulphate or surfactant. Subsequently, the membrane was removed from the water phase and the excess of aqueous solution at the under side thereof was removed with filtering paper. After a dripping period of about 7 minutes the membrane was transferred to an organic phase comprising toluene with dissolved therein 0.5%, by weight, above-mentioned prepolymer.

The membrane was held in the organic phase for 1 minute. Subsequently, the membrane was dried for 5 minutes at room temperature and thereafter 15 minutes in an air circulation oven at 90° C.

The reverse osmosis properties of this membrane were determined at room temperature at 40 bar in a solution comprising toluene and therein dissolved 1.0%, by weight, n-docosane (molar mass 310.6 dalton) with as result a toluene flux of 54 $l/m^2/h$ and a retention of docosane of 72%.

EXAMPLE II

In an analogous manner as described in example I a 2.97%, by weight, solution of a prepolymer was prepared from toluene diisocyanate (T-80) and a poly(tetramethylene ether glycol) (Polymeg 650$^R$, Quaker Oats Co.; OH contents 2.99 mmoles/g). Following the procedure of example I a composite membrane was prepared. The water phase contained 1.0%, by weight, of the amine. The organic phase comprised toluene with therein dissolved 0.5%, by weight, of above-mentioned prepolymer.

The reverse osmosis properties of this membrane were determined in an analogous manner as in example I with as result a toluene flux of 38 $l/m^2/h$ and a n-docosane retention of 85%.

EXAMPLE III

In an analogous manner as described in example I a 2.96%, by weight, solution of a prepolymer was prepared from 9.02 g poly(tetramethylene ether glycol) (Polymeg 1000$^R$), 2.03 g toluene diisocyanate (T-S0), i.e. molar proportion Polymeg 1000 / T-80=2/3 and 0.09 g $[CH_3(CH_2)_{10}CO_2]_2$ $Sn[(CH_2)_3CH_3]_2$ as catalyst. Following the procedure of example I subsequently a composite membrane was prepared. The organic phase comprised toluene with therein dissolved 2.0%, by weight, of above-mentioned prepolymer.

The reverse osmosis properties of this membrane were determined in an analogous manner as in example I with as result a toluene flux of 97 $l/m^2/h$ and a n-docosane retention of 74%.

EXAMPLE IV

One proceeds in the manner described in example III in the preparation of a composite membrane- The water phase contained 1.0%, by weight, of the amine. The organic phase contained 1.0%, by weight, of the prepolymer.

The reverse osmosis properties of this membrane were determined at room temperature at 40 bar in a 1.0%, by weight, solution of n-docosane and n-hexane with as a result n-hexane flux of 23 $l/m^2/h$ and a n-docosane retention of 83%.

EXAMPLE V

In an analogous manner as described in example I a 2.96%, by weight, solution of a prepolymer was prepared from toluene diisocyanate (T-80) and a poly(tetramethylene ether glycol) (Polymeg 2000$^R$, Quaker Oats Co.; OH contents 0.79 mmoles/g). Following the procedure of example I subsequently a composite membrane was prepared. The water phase contained 0.5% by weight of the amine. The organic phase comprised toluene with therein dissolved 1.0% by weight of above-mentioned prepolymer.

The reverse osmosis properties of this membrane were determined in an analogous manner as in example I with as result a toluene flux of 113 $l/m^2/h$ and a retention of n-docosane of 68%.

EXAMPLE VI

One proceeds in the manner described in example V in the preparation of a composite membrane. The water phase contained 1.0%, by weight, of the amine.

The reverse osmosis properties of this membrane were determined at room temperature at 40 bar in a 1.0%, by weight, solution of n-docosane in n-hexane with as result a n-hexane flux of 28 $l/m^2/h$ and a n-docosane retention of 85%.

EXAMPLE VII

In an analogous manner as described in example I a 3.0%, by weight, solution of a prepolymer was prepared from toluene diisocyanate (T-80) and polypropylene glycol (PPG 1000, Janssen Chimica, Belgium, OH contents 1.89 mmoles/g). Following the procedure of example I subsequently a composite membrane was prepared. The organic phase comprised toluene with therein dissolved 1.0%, by weight, of above-mentioned prepolymer.

The reverse osmosis properties of this membrane were determined in an analogous manner as in example I with as result a toluene flux of 40 $l/m^2/h$ and a n-docosane retention of 83%.

EXAMPLE VIII

In an analogous manner as described in example I a 3.26%, by weight, solution of a prepolymer was prepared from toluene diisocyanate (T-80) and a polybutadiene with final hydroxyl groups (PBD 2000, Poly Sciences; OH contents 1.25 mmoles/g). Following the procedure of example I subsequently a composite membrane was prepared. The water phase contained 1.0%, by weight, of the amine. The organic phase comprised toluene with therein dissolved 1.0%, by weight, of above-mentioned prepolymer.

The reverse osmosis properties of this membrane were determined in an analogous manner as in example I with as result a toluene flux of 17 $l/m^2/h$ and a n-docosane retention of 82%.

EXAMPLE IX

In an analogous manner as described in example I a prepolymer was prepared from 11.26 g $\alpha,\omega$-bis (3-hydroxylpropyl) poly(dimethyl siloxane) (Tegomer 2110$^R$, Th. Goldschmidt, West Germany; OH contents 1.21 mmoles/g), 4.75 g toluene diisocyanate (T-80), i.e. molar proportion Tegomer 2110 / T-80=½ and 0.11 g [CH$_3$(CH$_2$)$_{10}$CO$_2$]$_2$ Sn[(CH$_2$)$_3$CH$_3$]$_2$ as catalyst. The toluene was removed from the reaction mixture by means of vacuum distillation. Subsequently dry chloroform was added to the residue so that a 1.36%, by weight, solution of the prepolymer in chloroform was obtained. In an analogous manner as described in example I a composite membrane was prepared. The water phase comprised 1.0%, by weight, of the amine. The organic phase comprised chloroform with therein dissolved 1.36%, by weight, of above-mentioned prepolymer.

The reverse osmosis properties of this membrane were determined at room temperature at 40 bar in a 1.0%, by weight, solution of n-docosane in n-hexane with as result a n-hexane flux of 48 l/m$^2$/h and a n-docosane retention of 73%.

EXAMPLE X

In an analogous manner as described in example I a composite membrane was prepared wherein in the water phase 0.5%, by weight, H$_2$N—CH$_2$CH$_2$CH$_2$—NH—CH$_2$CH$_2$—NH—CH$_2$CH$_2$CH$_2$—NH$_2$, 0.05%, by weight, poly(vinyl alcohol) (Mowiol 4-88) and 0.04%, by weight, sodium dodecyl sulphate were used. The organic phase comprised toluene with therein dissolved 0.5%, by weight, toluene diisocyanate (T-80).

The reverse osmosis properties of this membrane were determined in an analogous manner as in example I with as result a toluene flux of 193 l/m$^2$/h and a n-docosane retention of 52%.

EXAMPLE XI

In an analogous manner as described in example I a composite membrane was prepared wherein in the water phase 0.2%, by weight, polyethylene imine M.W. 50.000–60.000, Aldrich, 0.05%, by weight, poly(vinyl alcohol) (Mowiol 4-88) and 0.04%, by weight, sodium dodecyl sulphate were used. The organic phase comprised toluene with therein dissolved 0.5%, by weight, toluene diisocyanate (T-80).

The reverse osmosis properties of this membrane were determined in an analogous manner as in example I with as result a toluene flux of 38 l/m$^2$/h and a n-docosane retention of 63%.

We claim:

1. A process for the separation of components in an organic liquid medium with a semi-permeable composite membrane with a porous carrier substrate on which a polymer network obtained by interfacial polymerization is applied, characterized in that the organic liquid medium is brought into contact with such semi-permeable composite membrane of which the polymer network is built from a reactive polyfunctional monomer having as reactive groups —NHR$_1$, wherein R$_1$ is hydrogen or a C$_1$-C$_{20}$ alkyl group, —OH or —SH and and one reactive polyfunctional monomer or oligomer or prepolymer or polymer having reactive —NCO groups built from a polyalkylene oxide with terminal —OH groups, either branched or not and either substituted or not, and an aromatic or aliphatic isocyanate with at least two —NCO groups.

2. The process of claim 1 characterized in that the polyalkylene oxide is poly(tetramethylene ether glycol) with the formula HO—(CH$_2$CH$_2$CH$_2$CH$_2$—)$_n$—H wherein n is an integral of $\geq 3$, preferably $\geq 6$.

3. The process of claim 1, characterized in that the polyalkylene oxide of the present invention is polypropylene glycol with the formula $$\text{HO}-(\text{CH}_2-\underset{\underset{\text{CH}_3}{|}}{\text{CH}}-\text{O})_n-\text{H}$$

wherein n is an integral of $\geq 3$, preferably 24 15.

4. A semi-permeable composite membrane with a porous substrate characterized in that a polymer network obtained by interfacial polymerization is applied on the carrier substrate, said polymer network being built from a reactive polyfunctional monomer having as reactive groups —NHR, wherein R$_1$ is H or a C$_1$-C$_{20}$ alkyl groups, —OH or —SH and a reactive polyfunctional monomer or oligomer or prepolymer or polymer having -NCO reactive groups built from a polyalkylene oxide with terminal —OH groups, either branched or not and either substituted or not, and an aromatic or aliphatic isocyanate with at least two —NCO groups.

5. A semi-permeable composite membranes of claim 4, characterized in that the polyalkylene oxide is poly(tetramethylene ether glycol) with the formula HO-(CH$_2$CH$_2$CH$_2$CH$_2$—O)$_n$—H wherein n is an integer of $\geq 3$, preferably $\geq 6$.

6. A semi-permeable composite membrane of claim 4, characterized in that the polyalkylene oxide is polypropylene glycol with the formula $$\text{HO}-(\underset{\underset{R_3}{|}}{\overset{\overset{R_2}{|}}{\text{Si}}}-\text{O})_n-\text{H}$$

wherein n is an integral of $\geq 3$, preferably $\geq 15$.

* * * * *

UNITED STATES PATENT AND TRADEMARK OFFICE
CERTIFICATE OF CORRECTION

PATENT NO. : 5,338,455
DATED : August 16, 1994
INVENTOR(S) : Dirk M. Koenhen, et al It is certified that error appears in the above-indentified patent and that said Letters Patent is hereby corrected as shown below:

Col. 5, l. 50, After Change "(FSO) to -- (T-80) --

Col. 7, lines 34-46, Cancel all of Example XI comprising all lines 34-46
Col. 8:

Col. 8, claim 2, line 13 correct the formula to read -- $HO-(CH_2CH_2CH_2CH_2-O)_n-H$ Claim 3, line 24, after "preferably", should read $\geq$ 15.

Claim 6, line 52. change "integral" to -- integer --.

Claim 6, lines 46-50, change the formula to read,
$$HO-(CH_2-CH-O)_n-H$$
$$\qquad\quad|$$
$$\qquad CH_3$$

Signed and Sealed this

Thirteenth Day of December, 1994

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,338,455
DATED : August 16, 1994
INVENTOR(S) : DIRK M. KOEHNEN et al It is certified that error appears in the above-indentified patent and that said Letters Patent is hereby corrected as shown below:

Front page, col. 1, item [21], correct the "Appl. No." to --711,166--

Signed and Sealed this

Twenty-seventh Day of December, 1994

Attest:

BRUCE LEHMAN

Attesting Officer

Commissioner of Patents and Trademarks